United States Patent [19]

Shih et al.

[11] Patent Number: 5,045,617

[45] Date of Patent: * Sep. 3, 1991

[54] ZWITTERION TERPOLYMERS OF A VINYL LACTAM, AN AMINO ALKYL ACRYLAMIDE OR ACRYLATE, AND A POLYMERIZABLE CARBOXYLIC ACID

[75] Inventors: Jenn S. Shih, Paramus; Terry E. Smith, Morristown, both of N.J.

[73] Assignee: ISP Investments Inc., Wilmington, Del.

[ * ] Notice: The portion of the term of this patent subsequent to Jan. 15, 2008 has been disclaimed.

[21] Appl. No.: 422,318

[22] Filed: Oct. 16, 1989

Related U.S. Application Data

[63] Continuation-in-part of Ser. No. 236,395, Aug. 25, 1988, Pat. No. 4,923,694.

[51] Int. Cl.$^5$ .................. C08F 26/10; C08F 226/10; C08F 220/10; C08L 39/00
[52] U.S. Cl. .................. 526/264; 525/326.9; 525/327.6; 524/548
[58] Field of Search .................. 526/264; 525/326.9

[56] References Cited

U.S. PATENT DOCUMENTS

| | | | |
|---|---|---|---|
| 4,237,253 | 12/1980 | Jacquet et al. | 526/75 |
| 4,521,404 | 6/1985 | Lorenz et al. | 424/71 |
| 4,767,613 | 8/1988 | Nuber et al. | 424/47 |
| 4,985,487 | 1/1991 | Shih et al. | 524/548 |

OTHER PUBLICATIONS

Ronald F. Brown, Organic Chemistry, [Wadsworth Publishing Company, Inc.], Belmont, Calif., 1975, page 669.

Allowed U.S. Application 07/236395 by Shih et al. Filing date: 08-25-88.

Primary Examiner—Joseph L. Schofer
Assistant Examiner—Wu C. Cheng
Attorney, Agent, or Firm—Walter Katz; Marilyn J. Maue; Joshua J. Ward

[57] ABSTRACT

The terpolymers of the invention:
(a) a vinyl lactam, such as vinyl pyrrolidone or vinyl caprolactam;
(b) an amino alkyl acrylamide or acrylate, such as dimethylaminopropyl methacrylamide or dimethylaminoethyl methacrylate; and
(c) a polymerizable carboxylic acid, such as acrylic acid or methacrylic acid.

The zwitterion terpolymers of the invention are made from the terpolymers by internal transfer of the proton of the carboxylic acid to the amino group of the acrylamide or acrylate monomer.

8 Claims, No Drawings

ZWITTERION TERPOLYMERS OF A VINYL LACTAM, AN AMINO ALKYL ACRYLAMIDE OR ACRYLATE, AND A POLYMERIZABLE CARBOXYLIC ACID

CROSS-REFERENCE TO RELATED PATENT APPLICATIONS

This application is a continuation-in-part of copending U.S. patent application Ser. No. 236,395, filed Aug. 25, 1988, by the same inventors.

BACKGROUND OF THE INVENTION

1. Field of the Invention

This invention relates to polymers, and more particularly, to zwitterion terpolymers useful in cosmetic formulations.

2. Description of the Prior Art

Cosmetic formulations containing copolymers of vinyl lactam and acrylate or methacrylate monomers are disclosed in U.S. Pat. Nos. 3,954,960 and 3,914,403. These copolymers provide excellent hair adhesion and set hold under conditions of high humidity; however, they are subject to excessive hydrolysis when formulated into cosmetic composition at a pH greater than 7 and/or maintained at an elevated temperature, for example, temperatures in excess of 40° C., for any considerable period of time.

U.S. Pat. No. 4,057,533 discloses that copolymers which contain vinyl lactam and quaternized aminomethyl acrylamide monomers are useful as flocculants and filler retention aids in paper-making.

Accordingly, an object of this invention is to provide new and useful polymers.

Another object is to provide zwitterion terpolymers for use in hair shampoo and conditioner formulations.

These and other objects and features of the invention will become apparent from the following description and disclosure.

SUMMARY OF THE INVENTION

Terpolymers are provided herein having the formula:

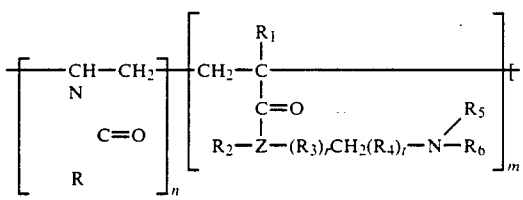

where R is alkylene having from 3 to 8 carbon atoms optionally substituted with lower alkyl; $R_1$ and $R_2$ are each independently hydrogen or methyl; $R_3$ and $R_4$ are each alkylene having from 1 to 18 carbon atoms optionally substituted with alkyl; the sum of r and t is one or two; $R_5$ and $R_6$ are each independently lower alkyl; Z is oxygen or nitrogen; if oxygen, $R_2$ is absent; M is a polymerizable carboxylic acid; n has a value of from 1 to 99 mole %; m has a Value of from 1 to 99 mole %; p has a value of from 1 to 99 mole %; the sum of $m+n+p$ is 100; preferably n is 50 to 90 mole %; m is 7 to 25 mole % and p 3 to 25 mole %.

The terpolymers of the invention thus comprise (a) a vinyl lactam, such as vinyl pyrrolidone or vinyl caprolactam;
(b) an amino alkyl acrylamide or acrylate, such as dimethylaminopropyl methacrylamide or dimethylaminoethyl methacrylate; and
(c) a polymerizable carboxylic acid, such as acrylic acid or methacrylic acid.

The zwitterion terpolymers of the invention are made from the terpolymers by internal transfer of the proton of the carboxylic acid to the amino group of the acrylamide or acrylate monomer.

The zwitterion terpolymers thus have both positive and negative charges in the molecule, a positive charge on the ammonium group and a negative charge on the carboxylate group, i.e.

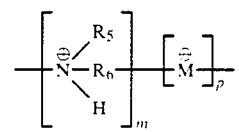

The polymers of the invention are made by solution polymerization or precipitation polymerization processes.

The terpolymers herein find particular application in cosmetic preparations, such as shampoo and hair conditioner products.

DETAILED DESCRIPTION OF THE INVENTION

The terpolymers of the invention are prepared by precipitation polymerization or solution polymerization of (a) a vinyl lactam, (b) an amino alkyl acrylamide or acrylate and (c) a polymerizable carboxylic acid, and recovering the terpolymer product.

Suitable vinyl lactam monomers for use herein have the formula:

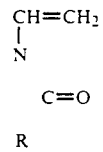

where R is as defined above.

Representative vinyl lactams include:
N-vinyl pyrrolidone
N-vinyl caprolactam
N-vinyl piperidone
4-methyl-N-vinyl pyrrolidone
3,5-dimethyl-N-vinyl caprolactam
N-vinyl-hexahydro-2-azepinone
N-vinyl-octahydro-2-azocinone
N-vinyl octahydro-2-azoninone and
N-vinyl decahydro-2-azecinone.

Of these, N-vinyl pyrrolidone, N-vinyl caprolactam and the ring substituted alkyl derivatives of the N-vinyl caprolactam and N-vinyl pyrrolidone monomers are preferred. N-vinyl-2-pyrrolidone is most preferred.

Suitable amino alkyl acrylamide monomers useful in preparing the terpolymers of the present invention include amino alkyl acrylamides and methacrylamides of the general formula:

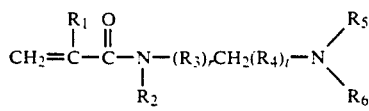

where $R_1$, $R_2$, $R_3$, r, $R_4$, t, $R_5$ and $R_6$ are as defined above.

Examples of amino alkyl acrylamides which are employed as monomers herein include:
N-[3-(dimethylamino) propyl]methacrylamide (DMAPMA)
N-[12-(dimethylamino) dodecyl]methacrylamide
N-[18-(dimethylamino) octadecyl]methacrylamide
N-[8-(dimethylamino) octyl]methacrylamide
N-[7-(dimethylamino) heptyl]acrylamide
N-[14-(dimethylamino) tetradecyl]acrylamide
N-[3-(dimethylamino) propyl]methacrylamide
N-[3-(diethylamino) propyl]acrylamide
N-{4-(dipropylamino) butyl]methacrylamide
N-[3-(methyl butyl amino) propyl]acrylamide
N-{2-[3-(dimethylamino) propyl]ethyl}acrylamide
N-{4-[4-(diethylamino) butyl]butyl}acrylamide.

Amino alkyl acrylate monomers useful in preparing the terpolymers of the invention have the formula:

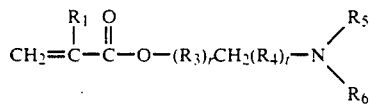

where $R_1$, $R_3$, r, $R_4$, t, $R_5$ and $R_6$ are as defined above.

Exemplary amino alkyl acrylates or methacrylates suitably employed in the production of the terpolymers of the present invention include:
dimethylaminomethyl acrylate
dimethylaminomethyl methacrylate
diethylaminomethyl acrylate
diethylaminomethyl methacrylate
dimethylaminoethyl acrylate
dimethylaminoethyl methacrylate (DMAEMA)
dimethylaminobutyl acrylate
dimethylaminobutyl methacrylate
dimethylaminoamyl methacrylate
diethylaminoamyl methacrylate
dimethylaminohexyl acrylate
diethylaminohexyl methacrylate
dimethylaminooctyl acrylate
dimethylaminooctyl methacrylate
diethylaminooctyl acrylate
diethylaminooctyl methacrylate
dimethylaminodecyl methacrylate
dimethylaminododecyl methacrylate
diethylaminolauryl acrylate
diethylaminolauryl methacrylate
dimethylaminostearyl acrylate
dimethylaminostearyl methacrylate
diethylaminostearyl acrylate
diethylaminostearyl methacrylate Suitable polymerizable carboxylic acid monomers for use herein include:
acrylic acid
methacrylic acid
maleic acid
itaconic acid
3-phenyl-2-propenic acid
crotonic acid and
fuaaric acid.

These monomers can polymerize with each other to form the desired terpolymer. In addition, the tertiary amino group of the terpolymer can accept the proton of the carboxylic acid group to form a zwitterion terpolymer having both a cationic ammonium group and an anionic carboxylate group. Thus, at about a pH of 7, this zwitterion terpolymer can exhibit amphoteric behavior, with both cationic and anionic moieties in the polymer. Furthermore, at about a pH>7, the polymer is only anionic, while at about a pH<7 the polymer is only cationic.

Accordingly, the terpolymers of the invention find particular application in hair preparation and styling formulations, such as shampoo and conditioner products, for the following reason Since hair normally is negatively charged, an anionic shampoo is desired for effective washing. However, for coating a film on hair with a conditioner, it is necessary to use a cationic polymer. In this invention, at about pH 7, the zwitterion terpolymer can function as both an anionic and cationic polymer, thus affording both shampoo and conditioner action within a single polymer Furthermore, when used in formulations having about a pH >7, it is an effective shampoo; while at having about pH<7, it is a useful conditioner.

The terpolymers of the present invention are conveniently prepared by subjecting a solution of the vinyl lactam, preferably vinyl pyrrolidone, the amino alkyl acrylamide or acrylate monomer, and the polymerizable carboxylic acid monomer, to conditions conducive to polymerization through double bonds. Thus, for example, the reaction can be suitably initiated by the action of free radicals, polymerization proceeding exothermically once initiated. Suitable free radical initiators conveniently employed and suitably utilized in accordance with the production of the copolymers of the present invention include organic and inorganic peroxide and perester compounds e.g., hydrogen peroxide, lauryl peroxide, decanoyl peroxide, di-tert-butyl peroxide, tert-butyl peroxypivalate, etc., aliphatic azo compounds, e.g., azobisisobutyronitrile, as well as other free radical initiators well known in the polymerization art.

The polymerization reaction of the present invention takes place in the presence of a solvent. Accordingly, any solvent which does not significantly interfere with polymerization of the monomers by chain transfer can be suitably employed. For solution polymerization process, the preferred solvents are the lower alcohols or water. However other solvents such as acetone, 2-butanone, etc. are also suitably employed for solution polymerization.

Preferably, precipitation polymerization is employed when it is desired to provide the terpolymer in powder form. On the other hand, solution polymerization is used when a solution of the terpolymer in the reaction solvent is advantageous.

Suitable solvents include aromatic, aliphatic and cyclic hydrocarbons, such as benzene, toluene, heptane, hexane and cyclohexane. Heptane and cyclohexane are preferred.

The polymerization reaction is effected at a temperature between about 40° C. and about 130° C. under from about 14 to about 50 psia. for a period of from about 1 to about 20 hours. To avoid run away conditions and to obtain a copolymer of a desirable high molecular weight it is preferred to carry out the polymerization at the lower end of the temperature range, e.g. between about 50° C. and about 80° C. The polymerization reaction is preferably carried out in the absence of free oxygen, conveniently under a blanket of an inert gas, such as nitrogen, argon or the like, and at atmospheric pressure.

The terpolymers of the invention can be made by precipitation polymerization or solution polymerization within the complete compositional range of monomer components. Accordingly, the terpolymers can be formed from 1-99% by weight of each of the monomer components.

Thus obtained via the above-described polymerization techniques as a powder or in solution form, the high molecular weight terpolymers herein are generally those having a Fikentscher K value (0.1N NaOH) within the range of 19 to 150 and more desirably within the range of 30 to 120, which corresponds approximately to a weight average molecular weight within the range of 15,000 to 5,000,000, and more desirably, within the range of 60,000 to 3,000,000.

The molecular weight of the copolymers of the present invention can be varied depending upon the particular choice of reactants, initiator, solvent and polymerization conditions, especially temperature, with the lower temperatures being conducive to the formation of higher molecular weight polymers.

In the preparation of the novel copolymers of the present invention, it is only necessary to mix the monomers in the ratios set forth above in order to provide a copolymer product produced through vinyl polymerization initiated by the action of free radicals. Generally, the copolymer is produced in a period of a few hours, e.g. less than about 10 hours.

Such terpolymers are eminently useful in baby shampoos because they do not irritate the eyes of the user, and in hair products, such as conditioners and shampoos, particularly in combination. The advantage of these polymers in such application is that the negatively charged portion of the polymer is effective for washing hair while the positive portion is effective for coating the hair with a film.

The present polymeric products are also useful as viscosity builders for cosmetic creams and lotions as well as for such hair treatment compositions to provide body and retentative moisturizing. When incorporated into standard formulations such as hair sprays, hair setting lotions, shampoos, hair and skin conditioners, and other personal care products, the amount of polymeric product used can range between about 0.05 weight % and about 8 weight %, based on total formulation. Usually not more than 4% is required to achieve the above desirable affects. The present polymer or polymer mixture is conveniently added to the cosmetic formulations as a powder or as an aqueous solution containing from about 10% to abut 30% of polymer.

The invention will now be described with reference to the following examples.

EXAMPLE 1

Preparation of Terpolymers of Vinyl Pyrrolidone (VP) Dimeathylaminopropyl Methacrylamide (DMAPMA) and Acrylic Acid (AA)

A. Precipitation Polymerization

A 1-liter, four-necked round bottom flask was equipped with thermometer, condenser, two dropping funnels and a mechanical stirrer. Vinyl pyrrolidone (80 g) and cyclohexane (510 g) were charged and heated to 60° C. with a $N_2$ purge. After heating for 30 minutes at 60° C., 7 drops of t-butyl peroxypivalate were added. Dimethylaminopropyl acrylamide (DMAPMA) (20 g) and acrylic acid (AA) (8.5 g) were charged separately into the dropping funnels, and both were added to the reaction flask during one hour. Then, one hour later, 6 drops of t-butyl peroxypivalate were added. The reaction mixture then was kept at 60°-65° C. for another 5 hours. The resulting precipitate was filtered, washed several times with cyclohexane and dried in an oven at 80° C.

B. Solution Polymerization

A 1-liter, four-necked round bottom flask was equipped with condenser, thermometer, dropping funnel and a mechanical stirrer 80 g of VP and 510g of deionized water were charged and heated to 60° C. with nitrogen purge. 20 g of DMAPMA and 8.5 g of AA were dissolved in 20 g of deionized water and transferred into the dropping funnel. After 30 minutes at 60° C., 7 drops of t-butyl peroxypivalate were added. The aqueous DMAPMA/AA solution was introduced slowly into the flask over a period of 45 minutes. After 75 minutes, 6 more drops of t-butyl peroxypivalate were added. The solution then was stirred at 60-65° C. for another 5 hours and cooled to room temperature.

EXAMPLE 2

Preparation of Terpolymers of VP/Dimethylaminoethyl Methacrylate (DMAEMA)/AA

Examples 1-A and 1-B were carried out using an equivalent amount of DMAEMA in place of DMAPMA to provide the corresponding terpolymers.

EXAMPLE 3

Preparations of Zwitterion Terpolymers of Invention

The terpolymers prepared above were dissolved in a buffered solution having a pH of 7. In this solution, amphoteric ionic behavior was observed, with both cationic and anionic characteristics being present in the polymer.

It is to be understood that the above examples are provided to illustrate specific and preferred embodiments of the invention and that many modifications and alterations can be made in these examples without departing from the scope of the invention.

What is claimed is:

1. A zwitterion terpolymer formed in aqueous solution from the terpolymer consisting essentially of the reaction product of:

(a) a vinyl lactam;

(b) an amino alkyl acrylamide or acrylate, and (c) a polymerizable carboxylic acid represented by the formula:

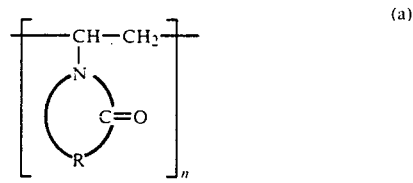

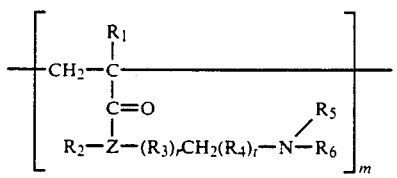

where R is alkylene having from 3 to 8 carbon atoms; $R_1$ and $R_2$ are each independently hydrogen or methyl; $R_3$ and $R_4$ are each alkylene having from 1 to 18 carbon atoms optionally substituted with alkyl; the sum of r and t is one or two; $R_5$ and $R_6$ are each independently lower alkyl; Z is oxygen or nitrogen; if oxygen, $R_2$ is absent; M is a polymerizable carboxylic acid; n has a value of from 1 to 99 mole %; m has a value of from 1 to 99 mole %; p has a value of from 1 to 99 mole %; the sum of m+n+p is 100 mole %; preferably n is 50 to 90 mole %; m is 7 to 25 mole % and p 3 to 25 mole % by internal transfer of the proton of the carboxylic acid group to the amino group of the acrylamide or acrylate group.

2. The terpolymer of claim 1 wherein R is alkylene having 3 to 5 carbon atoms.

3. The terpolymer of claim 1 wherein the amino alkyl acrylamide moiety has the formula:

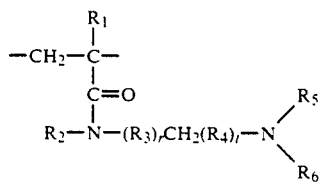

where $R_1$, $R_2$, $R_3$, r, $R_4$, t, $R_5$ and $R_6$ are as defined in claim 2.

4. The terpolymer of claim 3 wherein the amino alkyl acrylamide is selected from the group consisting of:
N-[3-(dimethylamino) propyl]methacrylamide;
N-[12-(dimethylamino) dodecyl]methacrylamide;
N-[18-(dimethylamino) octadecyl]methacrylamide;
N-[8-(dimethylamino) octyl]methacrylamide;
N-[7-(dimethylamino) heptyl]acrylamide;
N-[14-(dimethylamino) tetradecyl]acrylamide;
N-[3-(dimethylamino) propyl]methacrylamide;
N-[3-(diethylamino) propyl]acrylamide;
N-{4-(dipropylamino) butyl]methacrylamide;
N-[3-(methyl butyl amino) propyl]acrylamide;
N-(2-[3-(dimethylamino) propyl]ethyl}acrylamide; and
N-{4-[4-(diethylamino) butyl]butyl}acrylamide.

5. The terpolymer of claim 1 wherein the amino alkyl acrylate moiety has the formula

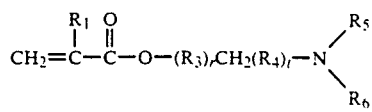

where $R_1$, $R_3$, r, $R_4$, t, $R_5$ and $R_6$ are as defined in claim 2.

6. The terpolymer of claim 5 wherein the amino alkyl acrylate is selected from the group consisting of
dimethylaminomethyl acrylate
dimethylaminomethyl methacrylate
diethylaminomethyl acrylate
diethylaminomethyl methacrylate
dimethylaminoethyl acrylate
dimethylaminoethyl methacrylate
dimethylaminobutyl acrylate
dimethylaminobutyl methacrylate
dimethylaminoamyl methacrylate
diethylaminoamyl methacrylate
dimethylaminohexyl acrylate
diethylaminohexyl methacrylate
dimethylaminooctyl acrylate
dimethylaminooctyl methacrylate
diethylaminooctyl acrylate
diethylaminooctyl methacrylate
dimethylaminodecyl methacrylate
dimethylaminododecyl methacrylate
diethylaminolauryl acrylate
diethylaminolauryl methacrylate
dimethylaminostearyl acrylate
dimethylaminostearyl methacrylate
diethylaminostearyl acrylate
diethylaminostearyl methacrylate.

7. The terpolymer of claim 1 wherein the polymerizable carboxylic acid group is derived from the group selected from acrylic acid, methacrylic acid, maleic acid, crotonic acid, 3-phenyl-2-propenic acid, furmaric acid and itaconic acid.

8. The polymer of claim 1 wherein n is 50 to 90 mole %; m is 7 to 25 mole %; and p is 3 to 25 mole %.

* * * * *